United States Patent [19]

Ohba et al.

[11] 4,169,140
[45] Sep. 25, 1979

[54] ANTIBIOTICS SF-1771 SUBSTANCE AND SF-1771-B SUBSTANCE AS WELL AS THE PRODUCTION OF THESE SUBSTANCES

[75] Inventors: Kazunori Ohba; Takashi Shomura; Hiroshi Watanabe, all of Yokohama; Kunikazu Totsukawa, Ohizumi; Michio Kojima; Shoji Omoto, both of Tokyo; Takashi Tsuruoka, Kawasaki; Shigeharu Inoue; Taro Niida, both of Yokohama, all of Japan

[73] Assignee: Meiji Seika Kaisha, Ltd., Kyobashi, Japan

[21] Appl. No.: 736,143

[22] Filed: Oct. 27, 1976

[30] Foreign Application Priority Data

Oct. 29, 1975 [JP] Japan .............................. 50-129306

[51] Int. Cl.² .............................................. A61K 35/00
[52] U.S. Cl. ..................................... 424/117; 424/123
[58] Field of Search ............................... 424/117, 123

[56] References Cited

U.S. PATENT DOCUMENTS 3,814,796  6/1974  Argoudelis et al. ................ 424/117

Primary Examiner—Jerome D. Goldberg
Attorney, Agent, or Firm—Haight & Huard

[57] ABSTRACT

A new antibiotic SF-1771 substance is produced by cultivating a new strain, *Streptomyces toyocaensis* SF-1771, in a liquid culture medium under aerobic conditions. This antibiotic may be isolated from the fermentation broth by treating the broth filtrate with a synthetic adsorbent resin for adsorption of the active compound and eluting the resin with an aqueous alcohol or aqueous acetone, followed by chromatographic purification. SF-1771 substance is a copper-containing antibiotic which shows antibacterial activity against *Escherichia coli, Salmonella typhi, Pseudomonas aeruginosa, Staphylococcus aureus* and *Bacillus subtilis*. Removal of the copper component from SF-1771 substance by treatment with hydrogen sulfide, an alkali metal sulfide or a copper-chelating agent gives SF-1771-B substance containing no copper component which shows antibacterial activity as high as but a toxicity lower than SF-1771 substance.

10 Claims, 6 Drawing Figures

WAVE LENGTH (nm)

ANTIBIOTICS SF-1771 SUBSTANCE AND SF-1771-B SUBSTANCE AS WELL AS THE PRODUCTION OF THESE SUBSTANCES

SUMMARY OF THE INVENTION

This invention relates to two new and useful antibiotics designated as SF-1771 substance and SF-1771-B substance. This invention further relates to the fermentation production of SF-1771 substance and the production of SF-1771-B substance by chemical treatment of SF-1771 substance as well as to the uses of SF-1771 and SF-1771-B substances.

BACKGROUND OF THE INVENTION

A great variety of pathogenic microorganisms such as bacteria and fungi are causative agents in producing diseases in man, animals and plants. Although a number of antibiotics have been developed, some of which possess usefully high antimicrobial activity against one or more pathogenic microorganisms, there remains a need for more effective agents to combat the many diseases caused by these microorganisms in man, animals and plants.

An object of this invention is to provide new antibiotics which are useful as antibacterial agents for therapeutic treatment of bacterial infections in man and animals and/or for sterilization of surgical materials and instruments. A further object of this invention is to provide processes for the production of these new antibiotics. Other objects of this invention will be clear from the following description.

We have made extensive research in an attempt to produce new and useful antibiotics. As a result, we have now found that when a new strain of the genus Streptomyces which was isolated from a soil sample collected in Tada-u-mi-cho, Takehara City, Hiroshima Prefecture, Japan, is cultivated in a culture medium under aerobic conditions, a substance exhibiting antibacterial activity against gram-negative and gram-positive bacteria is produced and accumulated in the culture. We have now succeeded in isolating this antibacterial substance from the culture and purifying it. As result of studies of the chemical, physical and microbiological properties of this isolated substance, it has been confirmed that this substance is a new antibiotic which is distinguishable from any of the known antibiotics. Thus, we have designated this new antibiotic as SF-1771 substance.

DETAILED DESCRIPTION OF THE INVENTION

Figure 2:
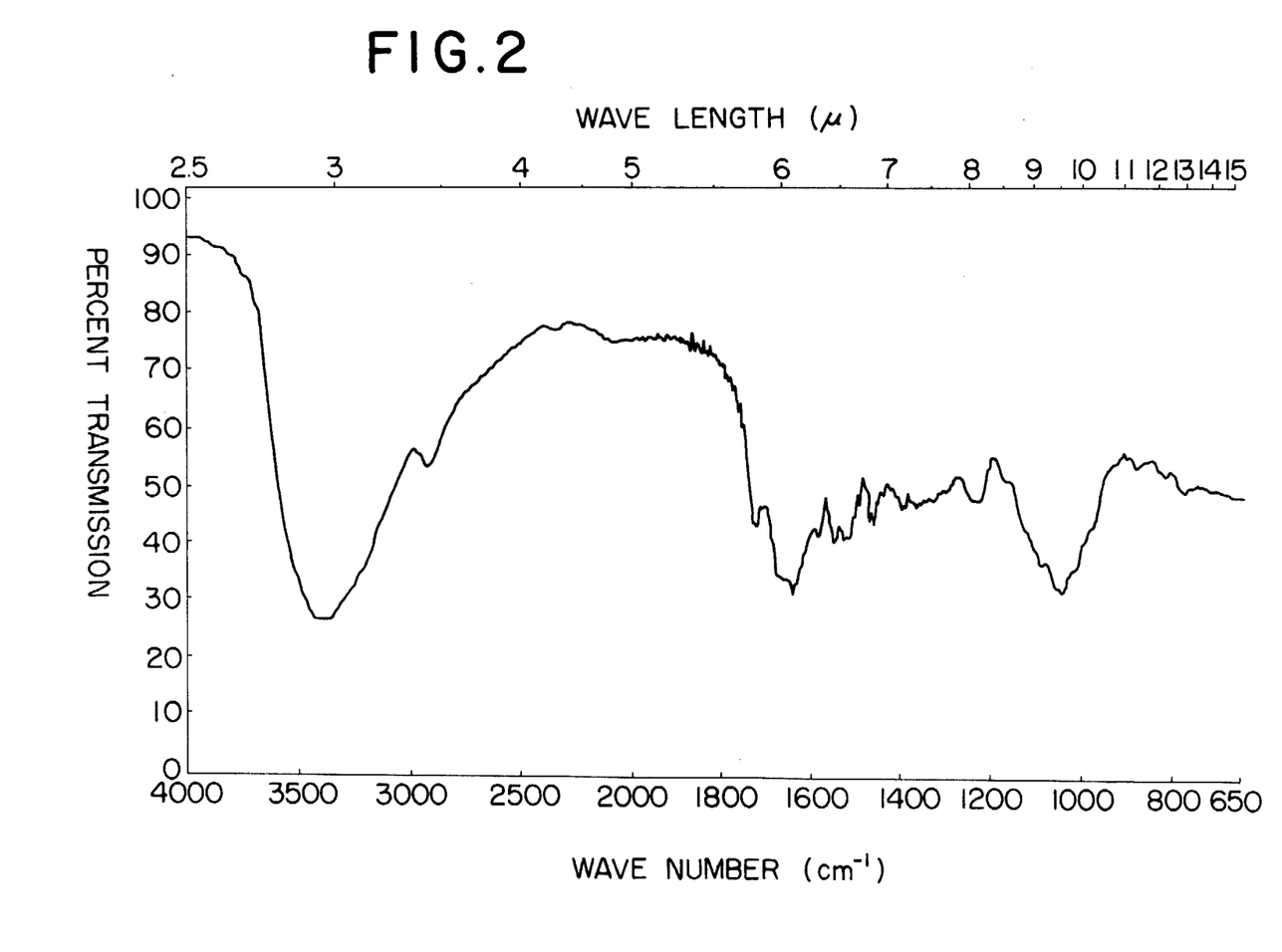
FIG. 2 shows an infra-red absorption spectrum of the SF-1771 substance hydrochloride pelleted in potassium bromide.

According to a first aspect of this invention, therefore, there is provided as a new and useful antibiotic SF-1771 substance, a blue-colored compound as an amorphous powder which is basic and soluble in water and shows an antibacterial activity, of which the hydrochloride discolors slowly into brown at 185° C. and decomposes at 208° C. with foaming, of which the hydrochloride is readily soluble in water, soluble in methanol, sparingly soluble in ethanol and butanol but insoluble in the other organic solvents, of which the hydrochloride is positive in the reactions with ninhydrin reagent, Ehrlich's reagent, potassium permanganate reagent, Greig-Leiback's reagent and is negative in the reaction with Sakaguchi's reagent, of which the hydrochloride shows a molecular weight of about 1600 as determined by Barger method and gives an elemental analysis C 38.70%, H 5.42%, N 13.03%, O 29.62%, S 3.62%, Cl 6.07% and Cu 3.53% (as measured by atomic absorption spectroscopy), of which the hydrochloride exhibits characteristic absorption peaks at 248 nm ($E_{1cm}^{1\%} = 146$) and at 282-284 nm ($E_{1cm}^{1\%} = 106$) in the ultra-violet absorption spectrum when dissolved in water and exhibits characteristic absorption bands as shown in FIG. 2 of the accompanying drawings in the infra-red absorption spectrum when pelleted in potassium bromide, and pharmaceutically acceptable acid-addition salts of said SF-1771 substance.

Examples of the pharmaceutically acceptable acid-addition salts of the SF-1771 substance according to this invention include the hydrochloride, sulfate, nitrate, phosphate, acetate, maleate, fumarate, succinate, tartrate, oxalate, citrate, methanesulfonate, ethanesulfonate and the like.

It has further been found that when the SF-1771 substance is treated with hydrogen sulfide or an alkali metal sulfide such as sodium sulfide in solution in water, the copper component present in the SF-1771 substance molecule is removed therefrom in the form of copper sulfide, so that there is produced a new further substance which does not contain the copper component but shows an antibacterial activity as high as but a toxicity lower than the SF-1771 substance itself. It has been found that the SF-1771-B substance also exhibits transplanted anti-tumor activity. Accordingly, this new further substance has been designated as SF-1771-B substance.

Figure 5:
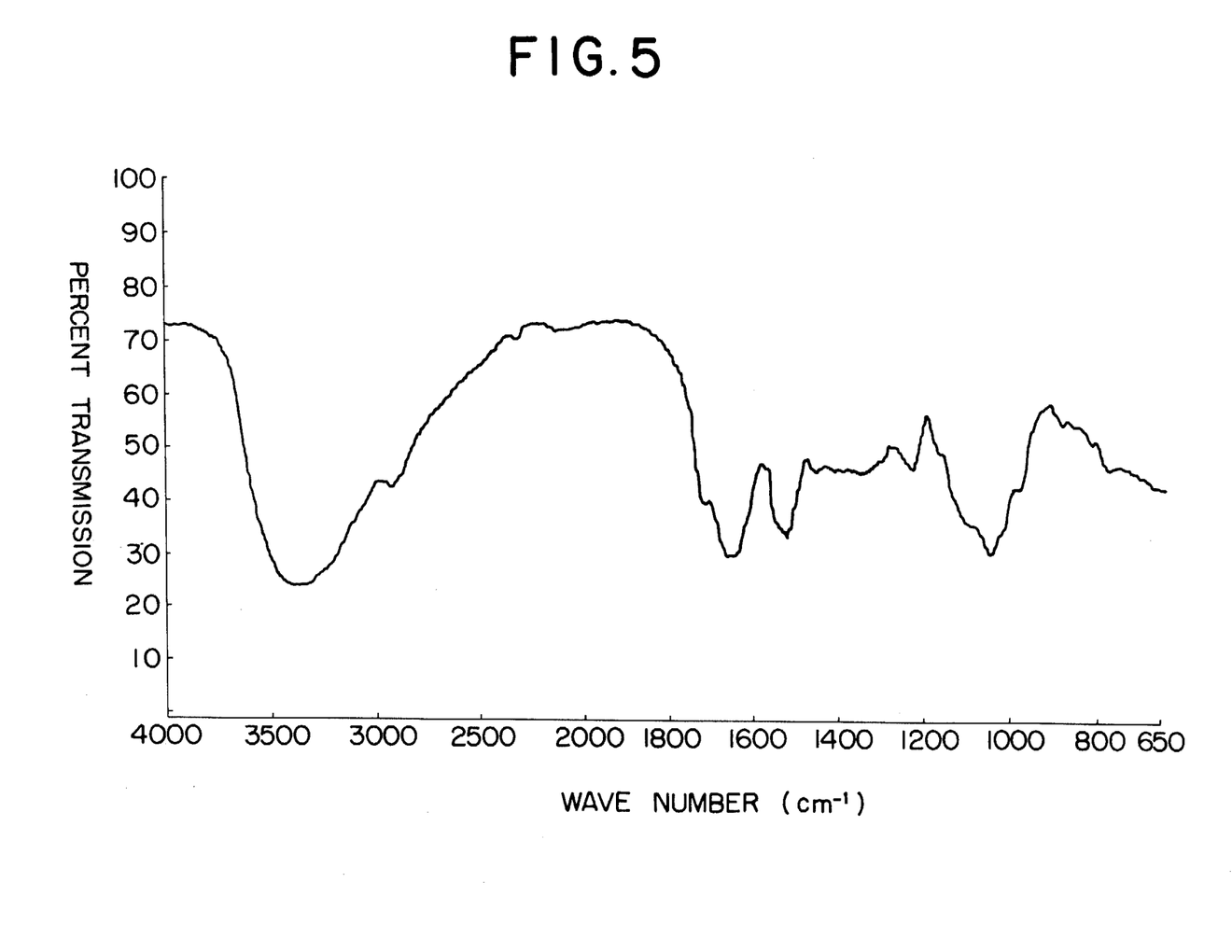
FIG. 5 shows an infra-red absorption spectrum of the SF-1771-B substance hydrochloride pelleted in potassium bromide.
Figure 6:
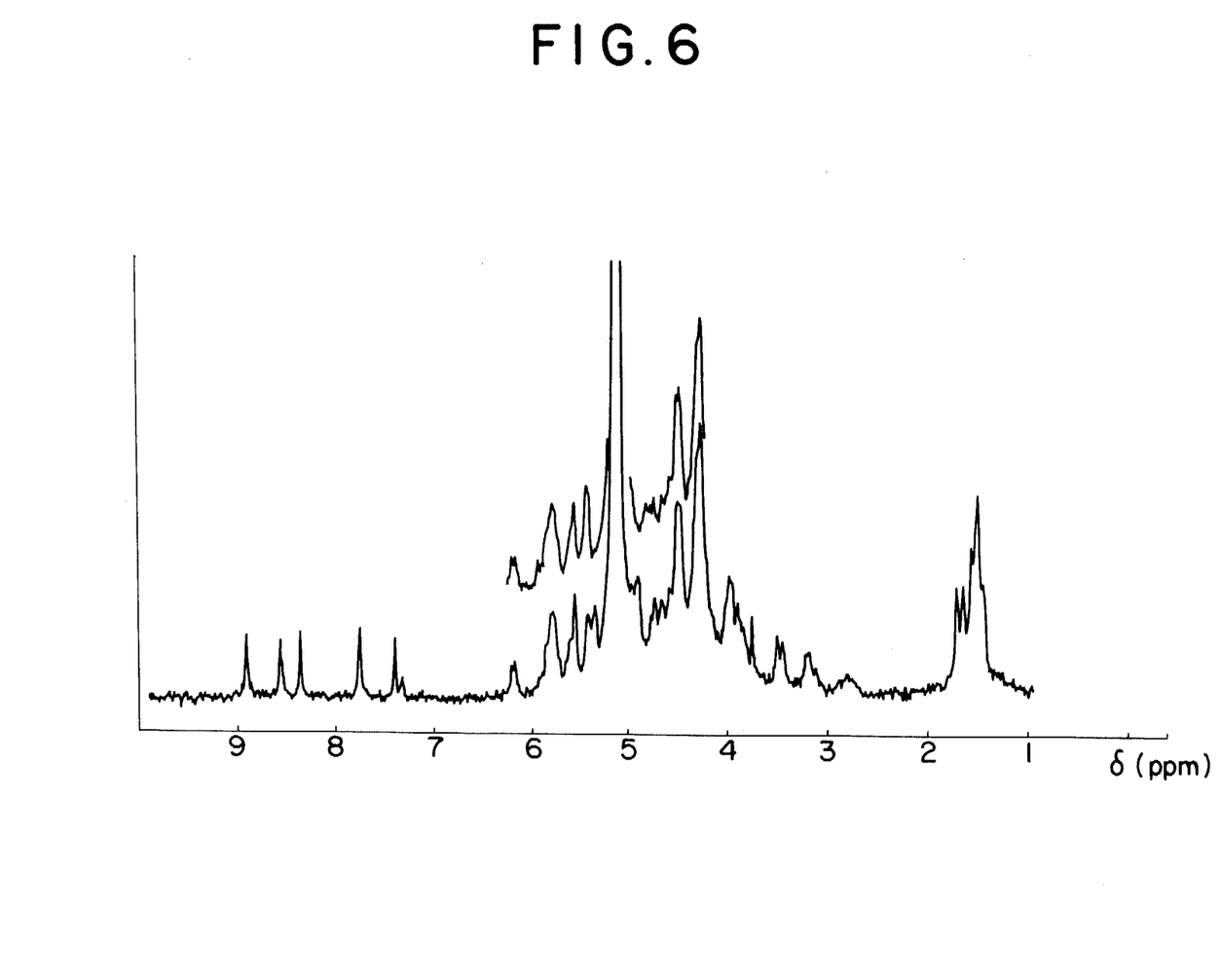
FIG. 6 shows a proton magnetic resonance absorption spectrum of the SF-1771-B substance hydrochloride in deutero-water as measured at 100 M Hz.

According to a second aspect of this invention, therefore, there is provided as a new and useful antibiotic, SF-1771-B substance, a colorless or faintly yellow-colored compound in an amorphous powder which is basic and soluble in water and shows an antibacterial activity and transplanted anti-tumor activity, of which the hydrochloride discolors into frown slowly at 180° C. and decomposes at 212° C. with foaming, of which the hydrochloride is readily soluble in water, soluble in methanol, sparingly soluble in ethanol and butanol but insoluble in the other organic solvents, of which the hydrochloride is positive in the reactions with ninhydrin reagent, Ehrlich's reagent, potassium permanganate reagent and Greig-Leiback's reagent and is negative in the reaction with Sakaguchi's reagent, of which the hydrochloride shows a molecular weight of about 1600 as measured by Barger method and a specific optical rotation $[\alpha]_D^{20} = -18.4°$ (c 1, $H_2O$), of which the hydrochloride shows an elemental analysis C 41.36%, H 5.53%, N 14.19%, S 3.64% and O 28.93%, of which the hydrochloride exhibits a characteristic absorption peak at 288-290 nm ($E_{1cm}^{1\%} = 84$) in the ultra-violet absorption spectrum when dissolved in water and exhibits characteristic absorption bands as shown in FIG. 5 of the accompanying drawings in the infra-red absorption spectrum when pelleted in potassium bromide and further exhibits a proton magnetic resonance absorption spectrum as shown in FIG. 6 of the accompanying drawings when dissolved in deutero-water, and pharmaceutically acceptable acid-addition salts of the SF-1771-B substance.

Examples of the pharmaceutically acceptable acid-addition salts of the SF-1771-B substance include those same as mentioned hereinbefore for the SF-1771 substance of this invention.

These acid-addition salts of the SF-1771-B substance as well as of the SF-1771 substance may be prepared by reacting the free base form of the SF-1771-B substance or the SF-1771 substance with a pharmaceutically acceptable acid such as hydrochloric acid, sulfuric acid, nitric acid, phosphoric acid or acetic acid in solution in water at ambient temperature in a known manner.

Referring to the accompanying drawings.

The SF-1771 substance hydrochloride shows the following physical and chemical properties:

(1) Appearance: Blue-colored amorphous powder.

(2) Decomposition temperature: Discoloration into brown takes place slowly at 185° C. and decomposition occurs at 208° C. with foaming.

(3) Elemental analysis: The SF-1771 substance hydrochloride contains the elements, carbon, hydrogen, nitrogen, oxygen, sulfur, copper and chlorine and gives an analysis result: C 38.70%, H 5.42%, N 13.03%, O 29.62%, S 3.62%, Cl 6.07% and Cu 3.53% (as measured by atomic absorption spectroscopy).

Figure 1:
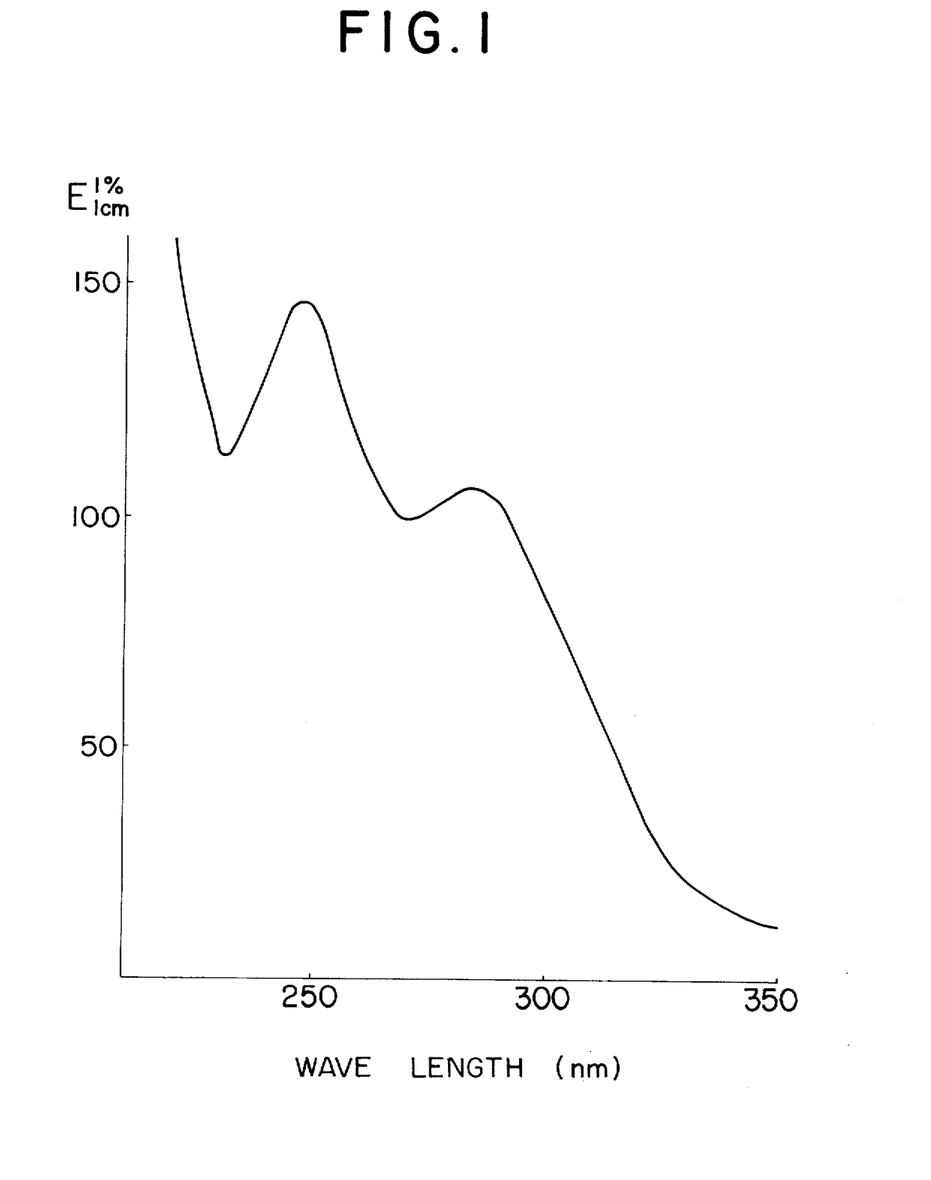
FIG. 1 shows an ultra-violet absorption spectrum of the SF-1771 substance hydrochloride in water.

(4) Ultra-violet absorption spectrum: The U.V. spectrum of the SF-1771 substance hydrochloride as measured for its aqueous solution is as shown in FIG. 1 and exhibits absorption peaks at 248 m$\mu$ ($E_{1cm}^{1\%} = 146$) and at 282-284 m$\mu$ ($E_{1cm}^{1\%} = 106$).

(5) Infra-red absorption spectrum: The I.R. spectrum of the SF-1771 substance hydrochloride as pelleted in potassium bromide is as shown in FIG. 2.

(6) Molecular weight: The molecular weight is about 1600, measured by Barger method and as assuming that a single copper atom is present per molecule of the SF-1771 substance.

(7) Solubility: Readily soluble in water, soluble in methanol, sparingly soluble in ethanol and butanol but insoluble in other organic solvents.

(8) Color reaction: Positive to ninhydrin, Ehrlich's, potassium permanganate and Greig-Leiback's reagents. Negative to Sakaguchi's reagent.

(9) Stability: Stable in neutral and acidic media, but relatively instable in alkaline media.

(10) Rf value: In a silica gel thin layer chromatography (on "Kieselgel 60 F$_{254}$", a product of E. Merck Co., Germany), the SF-1771 substance hydrochloride gives a single spot at Rf-values as shown in the following table.

Table 1

| Development solvents | Rf-value |
| --- | --- |
| Propyl alcohol-pyrionine-acetic acid-water (15:10:3:12 by volume) | 0.76 |
| Methanol-10% aqueous ammonium acetate-10% aqueous ammonia | 0.57 |

Table 1-continued

| Development solvents | Rf-value |
| --- | --- |
| (10:9:1 by volume) | |
| 10% Aqueous ammonium acetate-methanol (1:1 by volume) | 0.68 |
| 10% Aqueous ammonium acetate-methanol (1:2 by volume) | 0.54 |

(11) Rf value: In a paper chromatography (the ascending method), the single spot appears at Rf-values as shown in the following table.

Table 2

| Development solvents | Rf-value |
| --- | --- |
| Water-saturated n-butanol | 0 |
| 3% Aqueous ammonium chloride (by weight) | 0.71 |
| Phenol-water (3:1 by volume) | 0.69 |
| Acetone-water (1:1 by volume) | 0.09 |
| n-Butanol-methanol-water (4:1:2 by volume) | 0.06 |
| Benzene-methanol (4:1 by volume) | 0.02 |
| Water | 0.07 |

(12) Optical rotation: Determination of the specific optical rotation is impossible with the D-ray, owing to the blue color of the solution of the SF-1771 substance hydrochloride.

Figure 3:
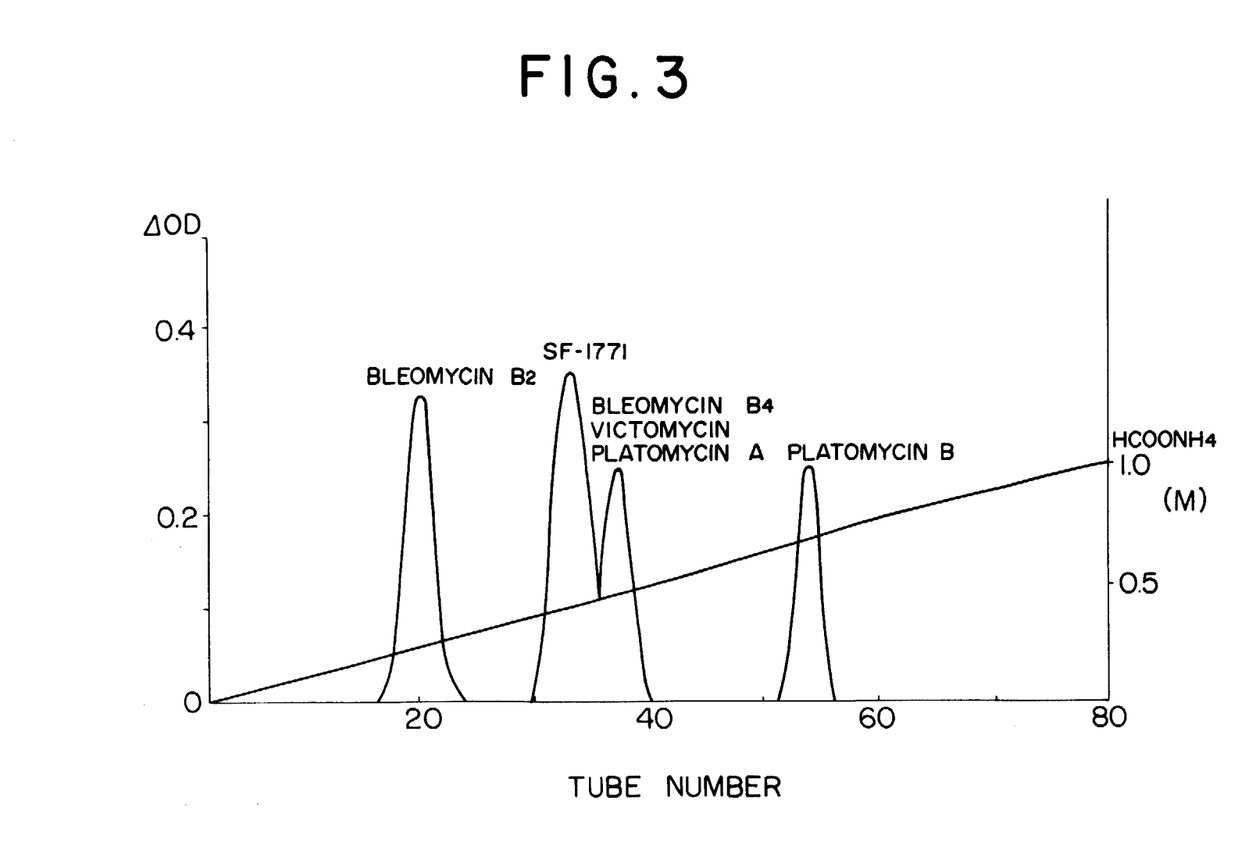
FIG. 3 shows patterns of gradient elution of the SF-1771 substance and its related antibiotics when chromatographed on a ion-exchange gel-filtration agent CM-Sephadex C-25 (H+), as compared to the elution pattern of ammonium formate.

(13) Elution pattern: FIG. 3 shows the gradient elution patterns of the SF-1771 substance hydrochloride and its related antibiotics when eluted from CM-Sephadex C-25 (H+) (an ion-exchange gel-filtration agent produced by Pharmacia Co., Sweden) developed with from 0 to 1.0 M ammonium fermate as the eluent. Each eluate was collected in 5 ml-fractions, and optical density of each fraction was determined. The difference between the determined values of the optical density of each fraction and the determined value of the optical density of the pure eluent were plotted as $\Delta$ OD along the ordinate, in relation with the number of the tube for each fraction plotted in the abscissa of the coordinate as shown in FIG. 3. The related antibiotics bleomycins, victomycin and platomycin A, B were tested for comparison purposes. From these elution patterns, it is seen that the SF-1771 substance hydrochloride is eluted later than bleomycin $B_2$ but somewhat faster than bleomycin $B_4$, victomycin and platomycin A.

The SF-1771 substance of this invention exhibits an antibacterial spectrum as shown in Table 3 below. The minimum inhibitory concentrations (M.I.C.) of the SF-1771 substance against various microorganisms were determined according to a known broth dilution method in such a manner that the determination was conducted after the incubation was effected at 37° C. for 18 hours using Heart Infusion Agar as the incubation medium.

Table 3

| Antibacterial spectrum of SF-1771 substance | |
| --- | --- |
| Test Microorganisms | M.I.C. ($\mu$g/ml) |
| Escherichia coli | 0.39 |
| Escherichia coli K-12-R | 0.39 |
| Salmonella typhi | <0.2 |
| Pseudomonas aeruginosa | 25 |
| Staphylococcus aureus 209P | 3.12 |
| Bacillus subtilis PCI-219 | 1.56 |

As will be seen from the results of Table 3, the SF-1771 substance of this invention exhibits a high antibacterial activity against both gram-positive and gram-negative bacteria, and it shows a remarkably high antibacterial activity against the gram-negative bacteria.

Moreover, it has been found that the SF-1771 substance also exhibits an antifungal activity against various fungi. The minimum inhibitory concentrations of the SF-1771 substance to various fungi were determined according to a known broth dilution method in such a manner that the determination was conducted after the incubation was effected at 28° C. for 3 days using Sabouraud glucose agar as the incubation medium. As exceptions, the incubation time was 5 days for *Trichophyton asteroides* and *Aspergillus fumigatus.* The antifungal spectrum of the SF-1771 substance is shown in Table 4 below.

Table 4

| Antifungal spectrum of SF-1771 substance | |
|---|---|
| Test organisms | M.I.C. (μg/ml) |
| *Candida albicans* | >100 |
| *Candida krusei* | 12.5 |
| *Candida parapsilosis* | 50 |
| *Candida stellatoidea* | 100 |
| *Candida tropicalis* | >100 |
| *Cryptococcus albidus* | 0.78 |
| *Cryptococcus laurentii* | 6.25 |
| *Cryptococcus neoformans* 301 | 0.78 |
| *Cryptococcus terreus* | 0.78 |
| *Cryptococcus uniguttulatus* | 3.13 |
| *Pichia spartinae* | 12.5 |
| *Saccharomyces cerevisiae* | 12.5 |
| *Trichophyton asteroides* | 6.25 |
| *Aspergillus fumigatus* | 1.56 |

Furthermore, it has been found that the SF-1771 substance is effective to treat the infections of Trichophytons in animals. Thus, six groups of test animals, each group consisting of 10 guinea pigs of Hartley-strain (male adult, weighing 310 to 400 g.), were inoculated with *Trichophyton asteroides* in such a way that the fur was cut off from four areas of the skin at the back of each animal, these skin areas were rubbed with sandpaper and an aqueous suspension of the mycelia of *Trichophyton asteroides* was then applied thereon. 2 Days after the inoculation, a solution of 1% by weight of the SF-1771 substance in ethanol was applied onto the inoculated skin areas once a day for 9 days for the therapeutic treatment of the Trichophyton infection. For the control group of test animals, only aqueous 70% ethanol was applied to the inoculated skin areas in the same way as above. After this treatment, the animals were sacrificed, and from the skin areas so treated were cut out three pieces (3×3 mm) of the skin which were subsequently incubated on a plate of agar culture medium at 27° C. for 3 days. Microscopic observation showed that no growth of the fungus could be observed on all the skin pieces which were cut out from the skin areas treated with the SF-1771 substance of this invention, whereas the growth of the fungus was observed on substantially all the skin pieces which were cut out from the skin areas of the control animals treated merely with the aqueous ethanol.

For determination of acute toxicity of the SF-1771 substance, solutions containing 6.25 mg–50 mg of the SF-1771 substance per 0.2 ml of isotonic sodium chloride solution were intravenously injected at a dose of 0.2 ml per mouse into several groups of mice, each group consisting of five mice of the ICR-strain (male adult weighing 20 g in average).

7 Days after this intravenous injection, it was estimated that percentages of the number of dead mice based on the whole number of mice tested were 100%, 100%, 60% and 20% at the dosages of 50 mg/kg, 25 mg/kg, 12.5 mg/kg and 6.25 mg/kg of the SF-1771 substance per mouse, respectively. Accordingly, the SF-1771 substance cannot be said to be non-toxic but is still useful for the sterilization of surgical materials and instruments as well as other devices and places which are desirably kept sterile. The SF-1771 substance may also be used as an antibacterial agent for external application. For these purposes, the SF-1771 substance may be formulated into an aqueous solution containing 0.01% to 0.1% by weight of the SF-1771 substance or an acid-addition salt thereof.

Comparison is now made between the SF-1771 substance and known water-soluble basic antibiotics. As water-soluble and basic antibiotics containing a copper constituent, there are known phleomycin (T. Ikekawa et al: "Journal of Antibiotics" Ser. A. Vol. 17, page 194 (1964)), bleomycins (H. Umezawa et al: "Journal of Antibiotics" Ser. A. Vol. 19, page 200 (1966)), zorbamycin and zorbonomycin B,C (A. D. Argoudelis et al: "Journal of Antibiotics" Vol. 24, page 543 (1971)), YA-56-X, YA-56Y substances (Y. Ito et al: "Journal of Antibiotics" Vol. 24, page 727 (1971)), victomycin (T. Nara et al: "Journal of Antibiotics" Vol. 28, page 366 (1975)), platomycin A,B (T. Nara et al: "Journal of Antibiotics" Vol. 28, page 662 (1975)), SS-70-A substance (Japanese patent application No. 86034/1974) and SS-70-B substance (Japanese patent application No. 86035/1974). All of these known copper-containing antibiotics show two absorption peaks, that is, the first one at 243–246 nm and the second one at 290–303 nm in their ultra-violet absorption spectra. However, bleomycins and phleomycin can be differentiated from each other and further can be differenctiated from the other, known copper-containing antibiotics. In contrast, the SF-1771 substance of this invention shows the first absorption peak at 248 nm and the second one at 282–284 nm in its ultra-violet absorption spectrum, indicating that the position of the absorption peaks of the SF-1771 substance is clearly different from the positions of the absorption peaks of the aforesaid known, water-soluble and basic copper-containing antibiotics. In this respect, the SF-1771 substance of this invention is a water-soluble and basic antibiotic of the peptide type but is differentiated from all the known water-soluble and basic copper-containing antibiotics as mentioned above. Therefore, it is evident that the SF-1771 substance is a new antibiotic compound which is distinct from any of the known antibiotics of the bleomycin and phleomycin types.

The SF-1771 substance of this invention may be produced by cultivating a strain of the genus Streptomyces which the present inventors firstly isolated from a soil sample collected in Tada-u-mi-cho, Takehara City, Hiroshima-Prefecture, Japan, as stated hereinbefore and which has now been designated as SF-1771 strain. The cultivation may be carried out under aerobic conditions in the same manner as in the production of known antibiotics by culturing known strains of the genus Streptomyces.

The SF-1771 strain has the following characteristics:
(I) Morphological observations Aerial mycelia are abundantly produced on glycerine asparagine agar, starch-agar, oatmeal-agar, yeast-malt-agar and tyrosine-agar, and the formation of spores is abundant. The mycelium produces monopodial branches but does not produce whorl.

The aerial mycelium bears spirals at the tip thereof. No formation of such special structure as a sclerotium is observed. Electron-microscopic observation shows that the surface structure of the spore is spiny. The spores are of elliptical shape to oval shape and normally measure 0.8–1.1 microns by 1.2–1.4 microns in size. Mature spore chains with more than 10 spores per chain are usually produced.

(II) Cultural characteristics on different culture media

The cultural characteristics are shown in Table 5 below. In the following table, the descriptions of colors given in a bracket [ are based on the standard of Color Harmony Manual by the Container Corporation of America.

Table 5

| Culture medium | Growth, color of reverse side | Aerial mycelium | Soluble pigment |
|---|---|---|---|
| Sucrose nitrate agar | Thin growth, colorless | Poor, white to grayish white | None |
| Glucose asparagine agar | Faintly yellow | Brownish gray [3ge] | None |
| Glycerine asparagine agar | Good growth, faintly yellow | Abundant, gray [2fe] | None |
| Starch agar | Good growth, faintly greyish yellow | Abundant, light yellowish brown [4ig] | None |
| Oatmeal agar | Good growth, grayish yellow | Abundant, light yellowish brown [4ig] | None |
| Yeast malt agar | Good growth, pale yellow to yellow | Cottony abundant, faintly brownish gray | None |
| Tyrosine agar | Good growth, grayish yellow | pale gray [2dc] | None |

Note:
The incubation temperature was 28° C. in general, unless stated otherwise.

(III) Physiological properties (1) Growth temperature range: The SF-1771 strain grows in a temperature range of 20°–38° C. on yeast-malt-agar medium.

(2) Liquefaction of gelatin: Gelatin is slowly liquefied by the incubation at 20° C. for 21 or more days.

(3) Hydrolysis of starch: Positive (at 28° C.).

(4) Coagulation of skimmed milk: Negative (at 28° C. and 37° C.).

(5) Peptonization of skimmed milk: Positive (at 28° C. and 37° C.).

(6) Chromogenicity: Negative.

(IV) Utilization of carbon sources (estimated in Pridham-Gottlieb's agar medium incubated at 28° C.)

(1) Utilizable: D-glucose, D-fructose, D-mannitol, I-inositol.

(2) Not utilizable: Sucrose, rhamnose, raffinose, L-arabinose, D-xylose.

The above-mentioned characteristics of the SF-1771 strain may be summarised as follows: The SF-1771 strain belongs to the genus Streptomyces, and the aerial mycelium produces spirals at the tip thereof and the surface structure of the spore is spiny. The SF-1771 strain shows good growth on various culture media, and the color of the reverse side of the growth is pale yellow to grayish yellow and is not tinged distinctively. The aerial mycelium is gray to brown in color, and no soluble pigment is produced on any culture medium.

The SF-1771 strain was designated as Streptomyces sp. SF-1771 and has been deposited in a Japanese public depository "Fermentation Research Institute", Chiba city, Japan, under deposit number FERM-P NO. 3253 (a culture sample of this strain was received by Fermentation Research Institute on September 18, 1975) and also in the "American Type Culture Collection", Rockville, Maryland, U.S.A., under ATCC number 31248.

As known strains similar to the SF-1771 strain, there may be mentioned *Streptomyces toyocaensis, Streptomyces natalensis, Streptomyces fasiculatus* and *Streptomyces alulus*.

In view of the descriptions of I.S.P. (International Streptomyces Project) in which reference is made to the articles of the "International Journal of Systematic Bacteriology" Vol. 18, pages 108–110, pages 174–176 (1968) and Vol. 22, pages 271–273, pages 323–326 (1972), these known four strains cannot be distinguished from the SF-1771 strain in their morphological properties and cultural characteristics. Thus, immediate comparison was made between the type cultures of these known four strains and the SF-1771 strain. As a result, it has been found that the SF-1771 strain is closest to *Streptomyces toyocaensis* amongst the above-mentioned known four strains and is distinguishable from the remaining known three strains. Closer comparison reveals that the SF-1771 strain is well coincident with the type culture of *Streptomyces toyocaensis* in many properties but is distinguishable from the latter in respect of the features shown in Table 6 below.

Table 6

| Features | SF-1771 strain | *Streptomyces toyocaensis* type culture |
|---|---|---|
| On oatmeal agar medium | | |
| Color of reverse side of growth | Grayish yellow | Yellow to brownish yellow |
| Soluble pigment | None | Pale yellow |
| On nutrient agar medium | | |
| Aerial mycelium | Cottony, pale gray | Poor (scant) |
| Antibiotic produced | SF-1771 substance | Toyocamycin |

Thus, the SF-1771 strain well coincides with *Streptomyces toyocaensis* in their principal properties, though distinction is observed in minor points. It appears reasonable, therefore, that the SF-1771 strain is identified to be a new strain of the known species *Streptomyces toyocaensis*. Accordingly, the SF-1771 strain is now designated as *Streptomyces toyocaensis* SF-1771.

The SF-1771 strain has properties which are liable to vary, as may usually be observed with the other species of Streptomyces. Thus, for instance, the SF-1771 strain may produce a variant or mutant when it is treated with various mutagens such as ultra-violet radiations, X-rays, radio active rays, high-frequency electromagnetic waves and chemicals. Any natural or artificial variant or mutant of the SF-1771 strain may be used for the production of the SF-1771 substance according to the concept of this invention, provided that it has the ability to produce the SF-1771 substance of this invention.

According to the third aspect of this invention, therefore, there is provided a process for the production of the SF-1771 substance, which comprises cultivating an SF-1771 substance-producing strain of the genus Streptomyces in a culture medium containing assimilable carbon and nitrogen sources under aerobic conditions for a sufficient time to produce and accumulate the SF-1771 substance in the culture medium and then recovering this antibiotic substance from the culture. According to a preferred embodiment of this third aspect of this invention, there is provided a process for the production of the SF-1771 substance, which comprises cultivating Streptomyces toyocaensis SF-1771 identified as FERM-P No. 3253 or ATCC. No. 31248 in a culture medium containing assimilable carbon and nitrogen sources under aerobic conditions for a sufficient time to produce and accumulate the SF-1771 substance in the culture medium and then recovering the SF-1771 substance from the culture.

In the process according to the third aspect of this invention for the production of the SF-1771 substance, the SF-1771 substance-producing strain and particularly Streptomyces toyocaensis SF-1771 strain may be cultivated in a known manner under aerobic conditions in a culture medium containing nutrients, namely such carbon and nitrogen sources which are assimilable by ordinary microorganisms. As the nutrients may be employed any of the known nutrient substances which have commonly been employed in the cultivation of the known strains of Streptomyces. For instance, glucose, sucrose, starch, glycerine, starch syrup, molasses, soybean oil and the like are useful as the carbon source. Soybean meal, wheatembryo, meat extract, peptone, dried yeast, corn steep liquor, ammonium sulfate, sodium nitrate and the like are useful as the nitrogen source. If required, inorganic salts such as calcium carbonate, sodium chloride, potassium chloride, phosphates and the like may be added to the culture medium. Furthermore, to the culture medium may be added such organic and inorganic material which aid the grouth of the SF-1771 substance-producing strain and promote the production of the SF-1771 substance. Copper sulfate may be added to the culture medium, but addition of a copper compound to the culture medium is not necessarily required because a trace of copper naturally occurring in the nutrient substances of natural origin employed in the culture medium is utilized by the SF-1771 strain as the copper source to produce the SF-1771 substance which is the copper-containing antibiotic.

As the method of cultivating the SF-1771 substance-producing strain, particularly the SF-1771 strain, liquid cultivation method and particularly submerged liquid cultivation method are most suitable, similar to the general processes of producing known antibiotics. The cultivation may suitably be effected under aerobic conditions and a suitable incubation temperature is in a range of 25° C. to 35° C. For the commercial or laboratory production of the SF-1771 substance, it is often preferred to carry out the cultivation at a temperature in the vicinity of 28° C. Under these cultivation conditions, the concentration of the SF-1771 substance in the culture broth reaches a maximum at the end of 2 to 8 days of fermentation, either in the shake-cultivation method or in the tank-cultivation method.

For assay of SF-1771 substance of this invention, the following assay method may be employed: Assaying culture medium comprising 0.5% polypeptone, 0.3% meat extract and 1.5% agar (pH 7.0) is used. As the assaying strain is used Escherichia coli NIH-J. In this assay method, at a concentration of 25 to 5 mcg/ml of the SF-1771 substance, the relation between the logarithm of the concentration of the SF-1771 substance and the diameter of the inhibition zone can be plotted linearly, giving an inhibition zone of 22.0 to 16.0 mm in diameter as determined by the paper-disc method.

As the SF-1771 substance of this invention is a water-soluble and basic substance of a peptide type containing the copper component as stated hereinbefore, it may usually be recovered from the culture broth by adsorbing on an inorganic adsorber such as active carbon and alumina or a synthetic adsorbent resin such as Amberlite XAD-2, Diaion HP-20, a weakly acidic ion-exchange resin, ion-exchange gel-filtration agent or gel-filtration agent, and then eluting from the adsorber with aid of a suitable eluent.

For the recovery and purification of the SF-1771 substance, however, the folllowing method is most efficient: The culture broth is filtrated with aid of a suitable filtration-aid such as diatomaceous earth to remove the mycelium and the other solid matter, and the broth filtrate so obtained is passed through a column of Amberlite XAD-2 (a synthetic adsorbent resin consisting of a microporous copolymer of styrene and divinylbenzene, a product of Rohm & Haas Co., U.S.A.), for the adsorption of the SF-1771 substance. The resin is then washed with water and eluted with an eluent of aqueous ethanol or aqueous acetone which may be adjusted to an acidic pH (pH 3.0 to 3.5) by addition of a mineral acid such as hydrochloric acid or an organic acid such as acetic acid. The eluate is collected in fractions, and the active fractions are combined together and, if necessary, neutralized. The active fractions are then concentrated under reduced pressure by distilling out the organic solvent (the ethanol or acetone). The resulting concentrated solution is passed through a column of CM-Sephdex C-25, (an ion-exchange gel-filtration agent consisting of a carboxymethyl-substituted cross-linked dextran gel, a product of Pharmacia Co., Sweden). The column is washed with water and then eluted with an aqueous solution of a suitable salt such as 0.2 M aqueous sodium chloride solution. The eluate is collected in fractions, and the active fractions are combined together and de-salted by treating with Amberlite XAD-2. The de-salted solution is concentrated under reduced pressure and freeze-dried to give a crude powder containing the SF-1771 substance. For the purification of this crude powder, said crude powder is taken up into a small volume of water and the aqueous solution is subjected to a column chromatography on Sephadex LH-20 (a product of Pharmacia Co., Sweden, a gel consisting of a derivative dextran sulfate) developed with methanol or a mixed solvent of butanol-methanol-water (4:1:2 by volume) as the eluent. The eluent is again collected in fractions, and the active fractions which give the single spot of a SF-1771 substance on paper chromatography are combined together and concentrated to dryness, affording a pure product of the SF-1771 substance as a blue-colored amorphous powder.

The SF-1771-B substance according to the second aspect of this invention may be produced by treating the SF-1771 substance with a suitable agent which is able to remove the copper component from the SF-1771 substance molecule. According to the fourth aspect of this invention, therefore, there is provided a process for the production of the SF-1771-B substance, which comprises subjecting the SF-1771 substance to a treatment for the removal of the copper component from the SF-1771 substance moluecule. The treatment for the removal of the copper component from the SF-1771 substance molecule may be effected either in such a manner that the SF-1771 substance in solution, in methanol or other suitable inert organic solvent is reacted with hydrogen sulfide or an alkali metal sulfide such as sodium sulfide and potassium sulfide for a sufficient time to remove the copper component from the SF-1771 substance molecule, or in such a manner that the SF-1771 substance is reacted with a copper-chelating agent such as 8-hydroxyquinoline and dithizone for a sufficient time to remove the copper component from the SF-1771 substance. When the SF-1771 substance is reacted with the copper-chelating agent for the removal of copper component therefrom, it is preferred that the SF-1771 substance dissolved in acidified water is reacted with a solution of dithizone in chloroform. These reactions for the removal of the copper constituent from the SF-1771 substance may be carried out at ambient temperature using as the reaction medium water or an organic solvent in which the reagents are soluble and which is inert to the reaction. According to a preferred embodiment of the fourth aspect of this invention, there is provided a process for the production of the SF-1771-B substance, which comprises subjecting the SF-1771 substance to a treatment with hydrogen sulfide, an alkali metal sulfide or a copper-chelating agent for a sufficient time to remove the copper component from the SF-1771 substance molucule.

The fourth aspect process of this invention for the production of the SF-1771-B substance may be effected not only using the SF-1771 substance which has been isolated in the form of a crude powder or a pure product as stated above, as the starting material which is to be treated with an agent for the removal of the copper component, but also using as the raw material the fermentation broth, the broth filtrate or a crude solution containing the SF-1771 substance dissolved therein, in such a way that the SF-1771 substance is reacted with hydrogen sulfide, an alkali metal sulfide or a copper-chelating agent while it is still present in the fermentation broth, the broth filtrate or the crude solution. To isolate the SF-1771-B substance from the reaction mixture is which the SF-1771 substance has been treated with the agent for the removal of the copper component therefrom, there may be employed such methods which are similar to those adoptable for the recovery of the SF-1771 substance from the culture of the SF-1771 substance-producing microorganism. Thus, the reaction mixture coming from the treatment of the SF-1771 substance for the removal of the copper component therefrom may be treated with Amberlite XAD-2 for the adsorption of the SF-1771-B substance, and the adsorbent resin may then be eluted, followed by chromatography of the active fractions of the eluate to give a crude powder containing the SF-1771-B substance. For further purification, this crude powder is chromatographed on a column of Sephadex LH-20 or Dianion HP-20 so that a pure product of the SF-1771-B substance is afforded. The SF-1771-B substance and the SF-1771 substance are water-soluble and basic antibiotics of the peptide type, and hence the SF-1771-B substance may generally be purified by a purification method which is analogous to such one for the purification of the SF-1771 substance.

The SF-1771-B substance hydrochloride shows the following physical and chemical properties, although some of these properties have been set out hereinbefore.

(1) Appearance: Colorless (white-colored) to slightly yellow colored amorphous powder.

(2) Decomposition temperature: Discoloration into brown takes place slowly at 180° C. and decomposition occurs at 212° C. with foaming.

(3) Elemental analysis: The SF-1771-B substance hydrochloride contains the elements, carbon, hydrogen, nitrogen, oxygen, sulfur and chlorine and gives an analysis result: C 41.36%, H 5.53%, N 14.19%, O 28.93% and S 3.64%.

It was noted that, upon the elemental analysis, the content of chlorine was 6.12%, although the determination of the chlorine content was difficult to carry out in an exact way owing to the presence of the sulfer component in the molecule.

Figure 4:
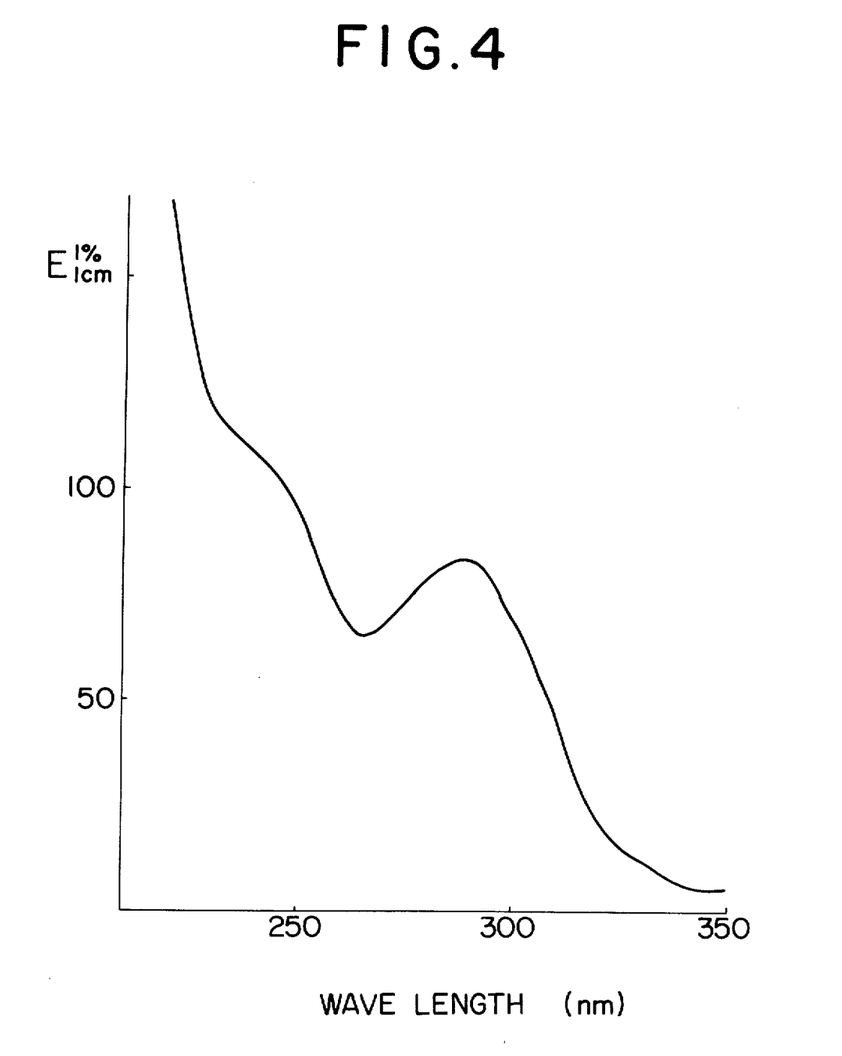
FIG. 4 shows an ultra-violet absorption spectrum of the SF-1771-B substance hydrochloride in water.

(4) Ultra-violet absorption spectrum: The U.V. spectrum of the SF-1771-B substance hydrochloride as measured for its aqueous solution is as shown in FIG. 4 and exhibits an absorption peak at 288–290 nm ($E_1^{1\%}{}_{cm} = 84$).

(5) Infra-red absorption spectrum: The I.R. spectrum of the SF-1771-B substance hydrochloride as pelleted in potassium bromide is as shown in FIG. 5.

(6) Proton magnetic resonance absorption spectrum: The P.M.R. spectrum of the SF-1771-B substance hydrochloride in deuterium oxide is shown in FIG. 6 as determined at 100 M Hz.

(7) Molecular weight: About 1600 as measured by the Barger method.

(8) Solubility: Soluble readily in water, soluble in methanol, sparingly soluble in ethanol and butanol but insoluble in the other organic solvents.

(9) Color reaction: Positive to ninhydrin, Ehrlich's, potassium permanganate and Greig-Leiback's reagents. Negative to Sakaguchi's reagent.

(10) Stability: Stable in neutral and acidic media but relatively instable in alkaline media.

(11) Rf value: In a silica gel thin layer chromatography (on "Kieselgel 60 $F_{254}$", a product of E. Merck Co., Germany), the SF-1771-B substance hydrochloride gives a single spot at Rf-values as shown in the following table. For comparison, the Rf-values for the SF-1771 substance hydrochloride are also shown in Table 7 below.

Table 7

| | Rf-value | |
|---|---|---|
| Development solvents | SF-1771-B | SF-1771 |
| Propyl alcohol-pyridine-acetic acid-water (15:10:3:12 by volume) | 0.76 | 0.76 |
| Methanol-10% aqueous ammonium acetate-10% aqueous ammonia (10:9:1 by volume) | 0.50 | 0.57 |
| 10% Aqueous ammonium acetate-methanol (1:1 by volume) | 0.48 | 0.68 |
| 10% Aqueous ammonium acetate-methanol (1:2 by volume) | 0.38 | 0.54 |

(12) Optical rotation: $[\alpha]_D^{20} = -18.4°$ (c 1, $H_2O$).

The SF-1771-B substance according to the second aspect of this invention exhibits an antibacterial spectrum as tabulated in Table 8 below. The minimum inhibitory concentrations (M.I.C.) of this substance against various microorganisms were determined according to a known broth dilution method in such a way that the determination was conducted after the incubation was effected at 37° C. for 18 hours using Heart Infusion Agar as the incubation medium.

Table 8

Antibacterial spectrum of SF-1771-B substance

| Test Microorganisms | M.I.C.(μg/ml) |
|---|---|
| *Escherichia coli* | 0.39 |
| *Escherichia coli* K-12-R | 0.39 |
| *Salmonella typhi* | 0.19 |
| *Pseudomonas aeruginosa* | 50 |
| *Staphylococcus aureus* 209P | 6.25 |
| *Bacillus subtilis* PCI-219 | 1.56 |
| *Salmonella pullorum* | 0.39 |
| *Pasturella* sp. 001 | 3.12 |
| *Pasturella* sp. 015 | 1.56 |
| *Pasturella* sp. 020 | 1.56 |

As will be seen from the result of Table 8, the SF-1771-B substance of this invention exhibits an antibacterial activity against the gram-negative and gram-positive bacteria substantially as high as that of the SF-1771 substance.

For estimation of acute toxicity of the SF-1771-B substance, solutions containing 6.25 mg–50 mg of the SF-1771-B substance per 0.2 ml of isotonic sodium chloride solution were intravenously injected at a dose of 0.2 ml per mouse into sevral groups of mice, each group consisting of five mice of the ICR-strain (male adult weighing 20 g in average). 7 Days after this intravenous injection, it was determined that percentages of the number of dead mice based on the whole number of mice tested were 100%, 60%, 0% and 0% at the dosages of 50 mg/kg, 25 mg/kg, 12.5 mg/kg and 6.25 mg/kg of the SF-1771-B substance per mouse, respectively. At the dose of 12.5 mg/kg of the SF-1771-B substance, all of the mice tested survived after the test, whereas at the dose of 12.5 mg/kg the number of mice corresponding to 60% of the whole number of the test mice died, and this reveals that the SF-1771-B substance has a significantly reduced acute toxicity as compared to the SF-1771 substance.

The SF-1771-B substance of this invention is considered to belong to the antibiotics of the bleomycin-phleomycin type. It is known that bleomycin can be inactivated by a crude enzyme solution consisting of a supernatant liquid which is obtained by centrifuging rat liver homogenate at 100,000 G.

In order to estimate to what extent the activity of the SF-1771-B substance of this invention can be inactivated in animals as compared to bleomycin $A_2$, the following test was made: Thus, 10 mg of the SF-1771-B substance as substrate was reacted at 37° C. with 2 ml of a crude enzyme solution (pH 7.2) which had been prepared from the rat liver homogenate in the above-mentioned way. At the end of 1 hour, 3 hours, 6 hours, 10 hours and 24 hours after the beginning of the enzymatic reaction, samples were taken out from the reaction mixture and assayed for their antibacterial potency against the assaying organism, *Escherichia coli* NIH-J. Percentages of the remaining antibacterial potency of these samples based on the initial antibacterial potency determined at the beginning of the reaction (the reaction time: 0 hour) were calculated. Degree of inactivation (%) was calculated by the following equation:

$$\left(1 - \frac{\text{Remaining Antibacterial Potency}}{\text{Initial Antibacterial Potency}}\right) \times 100$$

The results obtained are tabulated in Table 9 below.

Table 9

| Substrate | Degree of Inactivation (%) Reaction Time (hour) | | | | |
|---|---|---|---|---|---|
| | 1 | 3 | 6 | 10 | 24 |
| SF-1771-B | 0 | 0 | 20 | 48 | 72 |
| Bleomycin $A_2$ (decoppered derivative) | 24 | 36 | 60 | 66 | >94 |

From the results of the above table, it is presumed that the SF-1771-B substance is much more difficult to inactivate than bleomycin $A_2$ by the enzymatic reactions, so that the SF-1771-B substance is able to show a higher activity than bleomycin $A_2$ in vivo in animals.

Moreover, it has been found that the SF-1771-B substance of this invention exhibits an inhibitory activity to the growth of Hella S3 cells and shows a minimum degeneration concentration of 3.9 μg/ml against these cells under microscopic observation when incubated at 37° C. for 48 hours. Furthermore, the SF-1771-B substance exhibits an anti-tumor activity against Sarcoma 180 tumor cells. Thus, an aqueous suspension (0.05 ml) of Sarcoma 180 tumor cells was intraperitoneally inoculated into several groups of mice, each group consisting of five mice of the ICR-strain (male, about 8-weeks-aged) at a dosage of $10.4 \times 10^6$ cells per mouse. Twenty-four hours after the tumor inoculation (i.p.), 16 mg/kg, 8 mg/kg, 4 mg/kg, 2 mg/kg and 1 mg/kg of the SF-1771-B substance was dosed per mouse by intraperitoneal injection once daily for 3 days. For comparison, 40 mg/kg, 20 mg/kg, 10 mg/kg and 5 mg/kg of bleomycin were dosed into the comparative groups of mice in the same manner as the SF-1771-B substance. The 5 tumor-inoculated mice were used in each group. The mean number of survival days in the treated mice, the percentage increase in life span (abbreviated as I.L.S. %) to the control mice, and the ascites volume were measured to estimate the anti-tumor activity of the SF-1771-B substance and bleomycin. I.L.S. (%) was calculated by the following equation:

$$\left(\frac{\text{Mean survival days of the treated mice}}{\text{Means survival days of the control mice}} - 1\right) \times 100$$

The results are summarized in Table 10 below.

Table 10

| Test Compound | Dose (mg/kg) | Mean number of survival days | I.L.S. (%) | Ascites volume (ml) | 60-Days survivors |
|---|---|---|---|---|---|
| SF-1771-B | 16 | 8.8 | −50 | 0 | 0/5 |
| substance | 8 | 31.4 | 78.4 | 0.1 | 0/5 |
| | 4 | 36.8 | 109.1 | 13.0 | 0/5 |
| | 2 | 37.2 | 111.4 | 19.2 | 0/5 |
| | 1 | 29.0 | 64.8 | 21.8 | 0/5 |
| Bleomycin | 40 | 45.8 | 160.2 | 13.0 | 2/5 |
| (comparative) | 20 | 36.8 | 109.1 | 20.2 | 0/5 |
| | 10 | 35.0 | 98.9 | 21.4 | 0/5 |
| | 5 | 19.8 | 12.5 | 26.4 | 0/5 |
| Control | 0 | 17.6 | | 23.8 | 0/5 |

As shown in Table 10, it is seen that the dose of 2 mg/kg of SF-1771-B gives the maximum I.L.S. (111.4%), suggesting that an optimal effective dose of the SF-1771-B substance would be in a range of 2 to 4 mg/kg for therapeutic treatment of Sarcoma 180 tumor (ascites)-bearing mice, and that the SF-1771-B substance would be effective at lower doses than bleomycin.

Accordingly, the SF-1771-B substance of this invention is useful similarly to the bleomycin and may be formulated into known pharmaceutical forms and administered in the same manner as bleomycin.

In view of the antibacterial activity of the SF-1771 substance and the SF-1771-B substance, there is provided according to a further aspect of this invention an antibacterial agent comprising the SF-1771 substance or the SF-1771-B substance, or an acid-addition salt thereof, in combination with a carrier or vehicle therefor. According to another aspect of this invention, there is provided a pharmaceutical composition for therapeutic treatment of a living animal affected by a transplanted tumor, which comprises as the active ingredient the SF-1771-B substance or a pharmaceutically acceptable acid-addition salt thereof, in an amount sufficient to reduce the affection by the tumor cell in vivo, the active ingredient compound being in combination with a pharmaceutically acceptable carrier.

It will be appreciated that the actual preferred amounts of the SF-1771 substance and the SF-1771-B substance used will vary according to the particular composition formulated, the mode of application and the particular situs and organism being treated. Many factors that modify the action of the drug will be taken into account by the skilled in the art, for example, age, body weight, sex, diet, time of administration, route of administration, rate of excretion, drug combinations, reaction sensitivities and severity of the disease. Optimal application rates for a given set of conditions can be ascertained by the skilled in the art using conventional dosage determination tests in view of the above guidelines.

It is believed that using the preceding descriptions and without further elaboration, one skilled in the art can utilize the concept of this invention to its full extent. The following preferred specific embodiments are, therefore, to be construed as merely illustrative and not limitative of the remainder of the disclosure in any way.

DESCRIPTION OF THE PREFERRED EBODIMENTS

EXAMPLE 1

A culture medium (pH 7.0, 35 l.) comprising 4.0% sucrose, 1.0% soybean oil, 3.0% soybean meal, 2.0% wheat-embryo, 0.6% sodium chloride and 0.003% copper sulfate was charged into a jar-fermentor of 50 l. capacity and sterilized by heating. To this sterilized culture medium was inoculated a seed culture of *Streptomyces toyocaensis* SF-1771 strain (identified as FERM-P No. 3253 and as ATCC. 31248) which was previously incubated in slant agar medium. The inoculated culture medium was incubated at 28° C. for 114 hours under aeration and agitation (the speed of agitator 300 r.p.m.).

The fermentation broth so obtained was filtrated using diatomaceous earth as a filtration-aid, so that the broth filtrate (about 20 l.) was collected. This broth filtrate was passed through a column of 2 l. of adsorbent resin, Amberlite XAD-2 (a synthetic adsorbent resin consisting of a microporous copolymer of styrene and divinylbenzene, a product produced by Rohm & Haas Co., U.S.A.) for adsorption of the active substance by the resin. The resin was washed with 20 l. of water and then washed with 10 l. of 50% aqueous acetone (a mixture of acetone-water 1:1 by volume) and subsequently eluted with 50% aqueous acetone (pH 3, acidified by addition of hydrochloric acid) to effect the desorption of the active substance.

The eluate was collected in 500 ml-fractions, and the active fractions were combined together and neutralized by addition of 1 N aqueous sodium hydroxide, followed by concentration under reduced pressure to remove the acetone. The concentrated solution was then passed through a column of 250 ml of a gel-filtration agent CM-Sephadex C-25 (H$^+$) (a carboxymethyl-substituted cross-linked dextran gel, a product of Pharmacia Co., Sweden) for adsorption of the active substance. The gel column was washed with 215 l. of water and then with 0.5 l. of 0.1 M aqueous sodium chloride, followed by developement with 0.2 M aqueous sodium chloride. The eluate was collected in 18 ml-fractions, and it was found that the fractions No. 124 to No. 198 contained the active substance (the total volume of these active fractions was about 10 to 12-fold the volume of the CM-Sephadex gel). These active fractions were passed through a column of 100 ml of a synthetic adsorbent resin Diaion HP-20 (a microporous copolymer of styrene and divinylbenzene, a product of Mitubishi Kasei Co., Japan) for adsorption of the active substance. The resin was washed with 200 l. of water, followed by elution with 400 ml of 15% aqueous methanol (15% methanol in water) for the de-salting and by elution with 500 ml. of 30% aqueous methanol (30% methanol in water) for desorption of the active substance. The eluate was collected in 100 ml-fractions. The fractions No. 1 to No. 5 containing the active substance were combined together and concentrated to dryness under reduced pressure to give a green-colored crude powder of the SF-1771 substance.

This crude powder (320 mg) was taken up into 10 ml of water, and the resultant aqueous solution was passed through a column of 50 ml of CM-Sephadex C-25 (H$^+$) (a product of Pharmacia Co., Sweden) for adsorption of the active substance. The CM-Sephadex gel was washed with 500 ml of water and then developed with 0.15 M aqueous sodium chloride solution. The eluate was collected in 18 ml-fractions, and the active fractions (the fractions No. 82 to No. 122) were combined (the total volume of these active fractions was about 30-fold the volume of the CM-Sephadex gel) and then passed again through a column of 50 ml of a synthetic adsorbent resin Diaion HP-20 (the product of Mitsubishi Kasei Co., Japan) for adsorption of the SF-1771 substance. After washing with 100 of water, the resin was eluted with 100 ml of water and then with 100 ml of 15% aqueous methanol for the de-salting and finally eluted with 30% aqueous methnol for desorption of the SF-1771 substance. The eluate was collected in 35 ml-fractions, and the active fractions freed from the sodium chloride content (fractions No. 2 to No. 7) were combined and concentrated to dryness to give 42 mg of a greenish blue colored crude powder of the SF-1771 substance (about 60% purity).

This crude powder (42 mg) of the SF-1771 substance was taken up into 2 ml of 90% aqueous methanol (90% methanol in water) and the aqueous solution obtained was chromatographed on a column of 350 ml of a gel-filtration agent Sephadex LH-20 (a commerical product of Pharmacia Co., Sweden, a gel consisting of a derivative of dextran sulfate) developed with 90% aqueous methanol, so that 12 ml of the blue-colored active fraction was afforded. This blue-colored fraction was concentrated to dryness under reduced pressure to yield a blue-colored and pure product of the SF-1771 substance hydrochloride (containing the chelated copper component). Yield 24 mg.

EXAMPLE 2

(a) A culture medium (pH 7.0, 300 l.) comprising 4.0% sucrose, 1.0% soybean oil, 3.0% soybean meal, 2.0% wheat-embryo, 0.6% sodium chloride and 0.003% copper sulfate was placed into a jar-fermentor of 570 l. capacity and then sterilized by heating. To this sterilized culture medium was inoculated a culture of the SF-1771 strain (FERM-P No. 3253 and ATCC No. 31248) which was previously cultured in a 0.50 l. jar-fermenter. The incubation was carried out at 28° C. for 144 hours under aeration and agitation. The fermentation broth was filtrated using diatomaceous earth as a filtration-aid. The broth filtrate (about 190 l.) obtained was passed through a column of 18 l. of a synthetic adsorbent resin Amberlite XAD-2 (a product of Rohm & Haas Co., U.S.A.) for adsorption of the active substance. The resin was washed with 180 l. of water and then with 40 l. of 50% aqueous acetone (acetone-water, 1:1 by volume), followed by elution with 40 l. of 50% aqueous acetone (pH 3, acidified by addition of hydrochlodic acid). The eluate was collected in 5 l.-fractions, and the active fractions (fractions No. 3 to No. 9) were combined and neutralized by addition of 1 N aqueous sodium hydroxide and concentrated under reduced pressure by evaporation of the acetone.

The concentrated solution was passed through a column of 1 l. of a gel-filtration agent CM-Sephadex C-25 (a product of Pharmacia Co., U.S.A.) for adsorption of the active substance. The column was washed with 5 l. of water and then with 2 l. of 0.1 M aqueous sodium chloride solution, followed by development with 0.2 M aqueous sodium chloride solution so that the active substance was eluted out. The eluate was collected in 18 ml-fractions and the active fractions (fractions No. 82 to No. 240) were passed through a column of 1 l. of a synthetic adsorbent resin Diaion HP-20 (a product of Mitsubishi Kasei Co., Japan) for adsorption of the active substance, and this resin column was then washed with 2 l. of water for de-salting and then eluted with 1 l. of 30% aqueous methanol to effect desorption of the SF-1771 substance. The eluate was collected in 500 ml-fractions, and the active fractions (fractions No. 2 to No. 5) were again passed through a column of 200 ml of a gel-filtration agent CM-Sephadex C-25 (a product of Pharmaoia Co., Sweden) for adsorption of the active substance. The gel column was washed with water and then eluted with 0.2 M aqueous sodium chloride solution to effect the desorption of the SF-1771 substance. The eluate was collected in 18 ml-fractions and the active fractions (fractions No. 98 to No. 256) were passed through a column of 600 ml of Diaion HP-20 resin (a product of Mitsubishi Kasei Co., Japan) which was subsequently washed with 2 l. of water for de-salting and then eluted with 1 l. of 30% aqueous methanol to desorb the SF-1771 substance. The eluate was collected in 500 ml-fractions and the active fractions (fractions No. 3 to No. 5) were combined together, followed by concentration to dryness to give about 3 g. of a green-colored crude powder of the SF-1771 substance (48% purity).

This crude powder (3 g.) of the SF-1771 substance was taken up into 7 ml of 90% aqueous methanol, and the resulting methanolic solution was partition-chromatographed on a column of 1.5 l. of Sephadex LH-20 (a product of Pharmacia Co., Sweden) using a mixed solvent of butanol-methanol-water (4:1:2 by volume) as the developement solvent. The eluate was collected in 15 ml-fractions, and the blue-colored active fractions (fractions No. 32 to No. 44) were afforded. These active fractions combined together were concentrated to dryness in vacuo to give 1.2 g. of a partially purified powder of the SF-1771 substance (90% purity). This crude product of the SF-1771 substance (1.2 g.) was taken up into 6 ml of 90% aqueous methanol and the solution so obtained was chlomatographed on a column of 1.2 l. of Sephadex LH-20 using 90% aqueous methanol as the developement solvent. The eluate was collected in 16 ml-fractions and the blue-colored active fractions (fractions No. 26 to No. 31) were obtained in a total volume of 98 ml. These active fractions were combined together and concentrated to dryness in vacuo to give a pure product of the SF-1771 substance as a blue-colored amorphous powder. Yield 1 g. (b) This SF-1771 substance (150 mg) was dissolved in 15 ml of methanol, and into the resultant methanolic solution was passed gaseous hydrogen sulfide until the solution no longer showed the blue-color (for about 4 minutes). During this, a precipitate of copper sulfide deposited. The precipitate was filtered off and the filtrate was concentrated to a volume of about 4 ml under reduced pressure. The concentrated solution so obtained was chromatographed on a column of 1 l. of Sephadex LH-20 using 90% aqueous methanol as the developement solvent. The eluate was collected in 18 ml-fractions, and the active fractions (fractions No. 22 to No. 27) were obtained in a total volume of 112 ml. The combined active fractions were concentrated to dryness in vacuo, affording a pure product of the SF-1771-B substance as a white-colored amorphous powder. Yield 107 mg.

EXAMPLE 3

A culture medium (35 l., pH 7.0) comprising 4.0% sucrose, 1.0% soybean oil, 3.0% soybean meal, 2.0% wheat-embryo, 0.6% sodium chloride was placed in a jar-fermentor of 50 l. capacity. After sterilization of the culture medium by heating, the sterilized culture medium was inoculated with a seed culture of the SF-1771 strain (FERM-P No. 3253 and ATCC. 31248) which was previously incubated. The cultivation was made at 28° C. for 114 hours under aeration and agitation. The fermentation broth was filtered using diatomaceous earth as a filtration-aid, so that about 20 l. of the broth filtrate was obtained.

Gaseous hydrogen sulfide was passed through the broth filtrate for about 40 minutes at ambient temperature, and thereafter the reaction solution was purged by blowing air thereinto to strip off the excess of hydrogen sulfide from the reaction solution. The solution was then passed through a column of 2 l. of Amberlite XAD-2 (a product of Rohm & Haas Co., U.S.A.) for adsorption of the SF-1771-B substance. The resin column was washed with 20 l. of water and then with 10 l. of 50% aqueous acetone and finally eluted with 50% aqueous acetone (pH 3, acidified by addition of hydrochloric acid). The eluate was collected in 500 ml-fractions, and the active fractions (fractions No. 3 to No. 12) were combined together and neutralized by addition of 1 N aqueous sodium hydroxide. The neutralized solution was concentrated under reduced pressure by distilling off the acetone. The concentrated solution was passed through a column of 250 ml of CM-Sephadex C-25 (H+) (a product of Pharmacia Co., Sweden) for adsorption of the active substance. The column was washed with water and then eluted with 0.2 M aqueous sodium chloride solution for desorption of the active substance.

The eluate was collected in 18 ml-fractions, and the active fractions (fractions No. 68 to No. 126) were combined together, followed by treatment with 100 ml of a synthetic adsorbent resin Diaion HP-20 (a product of Mitsubishi Kasei Co., Japan) for adsorption of the SF-1771-B substance. The resin column was washed with 300 ml of water and then eluted with 500 ml of 60% aqueous methanol for desorption of the active substance. The active fractions of the eluate were combined together and concentrated to dryness to give 520 mg of a crude powder of the SF-1771-B substance. This crude product was further purified in the same manner as in Example 2, affording a pure product of the SF-1771-B substance. Yield 86 mg.

EXAMPLE 4

The SF-1771 substance hydrochloride (200 mg) was dissolved in 20 ml of 0.2% sodium sulfide solution in water and stirred for 10 minutes until the blue color had been changed into a dark brown color of the precipitated copper sulfide. The precipitated material was removed by filtration and discarded.

The filtrate was neutralized with 1 N hydrochloric acid and concentrated to a volume of 10 ml. The concentrated solution was desalted with Diaion HP-20 resin.

The eluate fractions were combined together, followed by concentration to dryness to give about 188 mg. of a colorless crude powder of the SF-1771-B substance.

EXAMPLE 5

The SF-1771 substance hydrochloride (350 mg) was dissolved in 30 ml of 0.1 N hydrochloric acid and extracted repeatedly with chloroform containing 0.5% dithiazon until no reddish violet color remaind.

After the chloroform phase was removed, the remaining aqueous solution was washed repeatedly with chloroform. The aqueous solution was neutralized with Amberlite IR-45 (OH—) (a product of Rohm and Haas Co., U.S.A.) and concentrated to dryness in vacuo, giving a crude yellowish powder (342 mg) of SF-1771-B substance. This product of SF-1771-B substance (342 mg) was taken up into 4 ml of 90% aqueous methanol and the solution so obtained was chromatographed on a column of 700 ml of Sephadex LH-20 using 90% aqueous methanol as the development solvent.

The eluate was collected in 10 ml-fractions, and the active fractions (fractions No. 30 to No. 36) were combined to a total volume of 72 ml and concentrated to dryness in vacuo to give a pure product of the SF-1771-B substance as a colorless amorphous powder. Yield 287 mg.

What we claim is:

1. A compound selected from the group consisting of SF-1771-B substance and the pharmaceutically acceptable acid addition salts thereof, the hydrochloride of which has the following properties:
  (a) slowly discolors from a colorless or faintly yellow-colored amorphous powder to brown at 180 degrees C. and decomposes at 212 degrees C. with foaming;
  (b) contains the elements carbon, hydrogen, nitrogen, oxygen, sulfur and chlorine giving an elemental analysis by atomic adsorption spectroscopy of about C 41.36%; H 5.53%; N 14.19%; O 28.93%; and S 3.64%.
  (c) an ultra-violet adsorption peak of an aqueous solution at 288–290 nm ($E_{1cm}^{1\%} = 84$);
  (d) an infrared adsorption spectrum pelleted in potassium bromide as shown in FIG. 5 of the accompanying drawings;
  (e) a proton magnetic resonance adsorption spectrum in deuterium oxide measured at 100 M Hz as shown in FIG. 6 of the accompanying drawings;
  (f) a molecular weight of about 1,600 as measured by the Barger method;
  (g) readily soluble in water, soluble in methanol, sparingly soluble in ethanol and butanol but insoluble in other organic solvents;
  (h) color reactions which are positive to ninhydrin, Ehrlich's, potassium permanganate and Greig-Leiback's reagents but negative to Sakaguchi's reagent; and
  (i) specific optical rotation $[alpha]_D^{20} = -18.4$ degrees (c=1, H$_2$O).

2. A process for preparing SF-1771-B substance according to claim 1, which comprises removing the copper component from SF-1711 substance, the hydrochloride of which has the following characteristics:
  (a) slowly discolors from a blue-color amorphous powder to brown at 185° C. and decompose at 212° C. with foaming;
  (b) contains the elements carbon, hydrogen, nitrogen, oxygen, sulfur, copper and chlorine giving and elemental analysis by atomic adsorption spectroscopy of about C 38.70%; H 5.42%; N 13.03%; O 29.62%; S 3.62%; Cl 6.07%; and Cu 3.53%;
  (c) an ultra-violet adsorption peaks of an aqueous solution at 248 nm ($E_{1cm}^{1\%} = 146$) and at 282–284 nm ($E_{1cm}^{1\%} = 106$);
  (d) an infrared adsorption spectrum pelleted in postassium bromide as shown in FIG. 2 of the accompanying drawings;
  (e) a proton magnetic resonance adsorption spectrum in deuterium oxide measurd at 100 M Hz as shown in FIG. 6 of the accompanying drawings;
  (f) a molecular weight of about 1,600 as measured by the Barger method;
  (g) is readily soluble in water, soluble in methanol, sparingly soluble in ethanol and butanol but insoluble in other conventional organic solvents; and
  (h) color reactions which are positive to ninhydrin, Ehrlich's, potassium permanganate and Greig-Leiback's reagents but negative to Sakaguchi's reagent
  wherein the SF-1771 substance is treated with hydrogen sulfide, sodium sulfide, potassium sulfide, 8-hydroxyquinoline or dithizone for a period of time sufficient to remove the copper component from the SF-1771 substance molecule, thereby forming said SF-1771-B substance.

3. A process according to claim 2, wherein a solution of SF-1771 substance in methanol is reacted with hydrogen sulfide by passing gaseous hydrogen sulfide into said solution.

4. A process according to claim 2, wherein SF-1771 substance present in the filtrate of a fermentation broth is reacted with hydrogen sulfide by passing gaseous hydrogen sulfide into said fermentation broth filtrate.

5. A pharmaceutical composition comprising a safe and effective antibacterial amount of a compound according to claim 1 in combination with a pharmaceutically acceptable carrier.

6. A method for inhibiting bacterial growth which comprises administering an antibacterially effective amount of a compound according to claim 1 to an animal susceptible thereto.

7. A method for inhibiting in vitro bacterial growth, which comprises contacting a surface susceptible to 8. A pharmaceutical composition comprising a safe and effective antifungal amount of a compound according to claim 1 in combination with a pharmaceutically acceptable carrier.

9. A method for inhibiting fungal growth which comprises administering an antifungally effective amount of a compound according to claim 1 to an animal susceptible thereto. said growth with an antibacterially effective amount of a compound according to claim 1.

10. A method for inhibiting in vitro fungal growth, which comprises contacting a surface susceptible to said growth with an antifungally effective amount of a compound according to claim 1.

* * * * *